(12) United States Patent
Berlin

(10) Patent No.: US 6,936,419 B1
(45) Date of Patent: Aug. 30, 2005

(54) OLIGOMER ARRAY WITH PNA AND/OR DNA OLIGOMERS ON A SURFACE

(75) Inventor: Kurt Berlin, Stahnsdorf (DE)

(73) Assignee: Epigenomics AG, Berlin (DE)

( * ) Notice: Subject to any disclaimer, the term of this patent is extended or adjusted under 35 U.S.C. 154(b) by 133 days.

(21) Appl. No.: 10/148,140

(22) PCT Filed: Nov. 24, 2000

(86) PCT No.: PCT/DE00/04301

§ 371 (c)(1),
(2), (4) Date: May 28, 2002

(87) PCT Pub. No.: WO01/38565

PCT Pub. Date: May 31, 2001

(30) Foreign Application Priority Data

Nov. 25, 1999 (DE) ................. 199 57 827

(51) Int. Cl.$^7$ ............. C07H 21/04; C21Q 1/68
(52) U.S. Cl. ............ 435/6; 435/287.2; 536/23.1; 536/24.3
(58) Field of Search ............... 435/6, 287.2; 536/23.1, 536/24.3

(56) References Cited

U.S. PATENT DOCUMENTS

| | | | |
|---|---|---|---|
| 5,474,796 A * | 12/1995 | Brennan .................... | 427/2.13 |
| 5,514,551 A * | 5/1996 | Yang et al. .................... | 435/6 |
| 5,589,330 A * | 12/1996 | Shuber .................... | 435/6 |
| 5,695,926 A * | 12/1997 | Cros et al. .................... | 435/5 |
| 6,214,556 B1 * | 4/2001 | Olek et al. .................... | 435/6 |
| 6,265,155 B1 * | 7/2001 | Meade et al. .................... | 435/6 |
| 6,605,432 B1 * | 8/2003 | Huang .................... | 435/6 |
| 6,664,045 B1 * | 12/2003 | Hyldig-Nielsen et al. ...... | 435/6 |

FOREIGN PATENT DOCUMENTS

| | | |
|---|---|---|
| WO | WO 93/25563 A1 | 12/1993 |
| WO | WO 97/46705 A1 | 12/1997 |
| WO | WO 99/28498 A2 | 6/1999 |
| WO | WO 01/27317 A2 | 4/2001 |

OTHER PUBLICATIONS

Ugozzoli et al. "Detection of specific alleles by using allele-specific primer extension followed by capture on solid support." GATA, vol. 9, No. 4, pp. 107-112, 1992.*
Cronin et al. "Cystic fibrosis mutation detection by hybridization to light-generated DNA probe arrays." Human Mutation, vol. 7 pp. 244-255, 1996.*
Gwynne et al., "Microarray Analysis: the next revolution in molecular biology," www.sciencemag.org/feature/e-market/benchtop/micro.shl.

* cited by examiner

Primary Examiner—Jeanine A. Goldberg
(74) Attorney, Agent, or Firm—Kriegsman & Kriegsman

(57) ABSTRACT

An oligomer array with PNA (peptide nucleic acid) and/or DNA oligomers on a surface is described, which comprises oligomers of between 6 and 20 monomers or nucleobases each, whereby each of these contains at least one sequence of the general formula DDCGDD or of the general formula DDTGDD or of the general formula HHCGHH or of the general formula HHCAHH, wherein H indicates one of the bases: adenine (A), cytosine (C), or thymine (T) and D represents one of the bases: adenine (A), guanine (G) or thymine (T), and wherein the site of the oligomers on the surface is correlated with the sequence of the oligomers.

Figure 1:
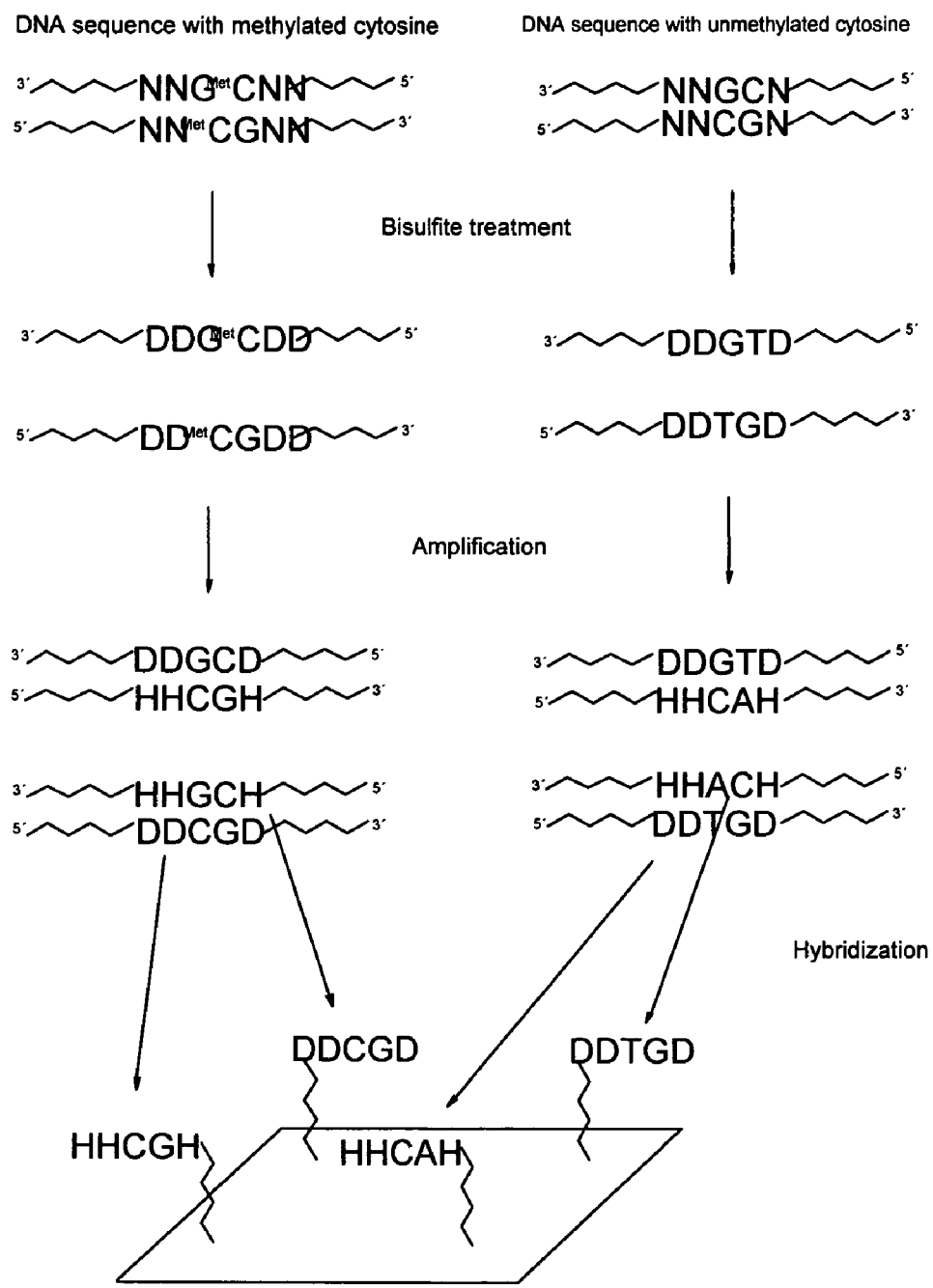

The oligomer arrays according to the invention are used for the detection of cytosine methylations in genomic DNA.

9 Claims, 1 Drawing Sheet

OLIGOMER ARRAY WITH PNA AND/OR DNA OLIGOMERS ON A SURFACE

The invention concerns an oligomer array with PNA (Peptide Nucleic Acids) and/or DNA oligomers on a surface.

The planes of observation that have been well studied in recent years in molecular biology according to developments in methods include the genes themselves, the [transcription and] translation of these genes into RNA and the proteins formed therefrom. In the course of development of an individual, when and which gene is turned on and the control of how specific genes are activated and inhibited in specific cells and tissues, can be correlated with the extent and nature of the methylation of the genes or of the genome. On this basis it is hypothesized that pathogenic states are expressed by a modified methylation pattern of individual genes or of the genome.

5-Methylcytosine is the most frequent covalently modified base in the DNA of eukaryotic cells. For example, it plays a role in the regulation of transcription, genomic imprinting and in tumorigenesis. The identification of 5-methylcytosine as a component of genetic information is thus of considerable interest. 5-Methylcytosine positions, however, cannot be identified by sequencing, since 5-methylcytosine has the same base-pairing behavior as cytosine. In addition, in the case of a PCR amplification, the epigenetic information that is borne by the 5-methylcytosines is completely lost.

The modification of the genomic base cytosine to 5'-methylcytosine represents the most important and best-investigated epigenetic parameter up to the present time. However, even though there are methods presently known for determining complete genotypes of cells and individuals, there are still no comparable approaches to generate and evaluate epigenotypic information on a large scale.

A relatively new method that in the meantime has gained widespread application for investigating DNA relative to 5-methylcytosine is based on the specific reaction of bisulfite with cytosine, which after subsequent alkaline hydrolysis, is converted to uracil, which corresponds to thymidine in its base-pairing behavior. 5-Methylcytosine, in contrast, is not modified under these conditions. Thus the original DNA is converted in such a way that methylcytosine, which initially cannot be distinguished from cytosine by its hybridization behavior, now can be detected as the only remaining cytosine, by "standard" molecular-biological techniques, for example, by amplification and hybridization or sequencing. All of these techniques are based on base-pairing, which can now be fully utilized. The prior art, which concerns sensitivity, is defined by a method, which incorporates the DNA to be investigated in an agarose matrix, so as to prevent the diffusion and renaturation of DNA (bisulfite reacts only on single-stranded DNA) and replaces all precipitation and purification steps by rapid dialysis (Olek, A. et al., Nucl. Acids. Res. 24, 5064–5066.) Individual cells can be investigated with this method, which illustrates the potential of the method. Of course, previously only individual regions of up to approximately 3000 base pairs long have been investigated; a global investigation of cells for thousands of possible methylation events is not possible. Of course, this method cannot analyze very small fragments from small sample quantities in a reliable manner. These are lost despite the protection from diffusion through the matrix.

A review of additional known possibilities for detecting 5-methylcytosines may also be derived from the following review article: Rein, T., DePamphilis, M. L., Zorbas, H., Nucleic Acids Res. 26, 2255 (1998).

There are basically several possibilities for preparing oligomer arrays on the most varied surfaces:

1. All oligomers are prepared in the conventional manner individually and in relatively large quantity in the test tube or in special automatic synthesis devices and then pipetted individually onto the carrier. For this purpose, usually automatic, highly precise micropipetting robots are used. The advantage of this method is that it is extensively based on already optimized standard methods and equipment. In this way, qualitatively superior DNA arrays with very pure oligomers can be prepared, which has an extremely positive influence on the detection sensitivity and reliability that can be obtained with the array. The great disadvantage of the method is that it is enormously time-consuming and thus expensive. It is applied particularly to the synthesis of individual oligomers.

2. The oligomers are synthesized directly on the substrate by pipetting of minute quantities. The oligomer chain provided therein is built up nucleotide by nucleotide at each grid point. For pipetting, as in method 1), a specialized micropipetting robot, or. e.g., a device which contains channels for introducing the individual synthesis bases at the respective points on the array (EP-A 0915897) is utilized. The chemical synthesis method is basically the same as in the case of conventional oligomer synthesis in automatic synthesis devices. The difference is that all oligomers are prepared simultaneously, independent of their number, by a single automatic device directly at the determination site provided.

The separate working steps in method 1) of oligomer synthesis and micropipetting are now combined into a single working step. The expenditure for equipment and manual labor is thus considerably reduced in comparison to method 1).

3. As in method 2), the oligomers are synthesized directly on the substrate, but the targeted binding of the correct nucleobases at the correct grid points is done by a completely parallel photolithographic technique originating from semiconductor manufacture, instead of sequential, target-precise pipetting steps. The method is based on the fact that one can remove, with light of a specific wavelength and in a targeted manner, the 5'-OH protected groups of oligonucleotides. By suitable local irradiation patterns, one can thus make oligonucleotide ends reactive at precisely those grid points, at which one wishes to bind a new nucleotide building block in the next step. With complete wetting of the array surface with a solution of the nucleotide building blocks, a nucleobase is bound only to the previously exposed sites; all of the unexposed sites remain unchanged. The local exposure patterns are produced by positioning a photomicrographic black-and-white mask between the substrate and the light source, which covers all of the grid sites, which are not to be made reactive. The elongation of the oligomer chains on all grid points by one nucleobase is conducted as follows: With the help of a first mask, precisely those grid points are exposed, which must be extended by the first of four possible types of nucleobases (e.g., C). Accordingly, the array is wetted with a solution of the corresponding nucleotide building block, whereby only the exposed points are extended by this base. Since the newly bound nucleotide building blocks are still all present with a protective group, they are not further reacted in the following steps, until their protective groups are cleaved by another exposure. After this reaction step, the array is washed. Now, precisely those grid sites, which must be extended by the second of the four possible nucleobases (e.g., T) are exposed by means of a second mask. Then the array is again wetted with a solution of the corresponding nucleotide building block and the exposed sites are thus extended by this base. The method is conducted in the same way for the remaining two nucleobases (G and A). In order to extend all oligomers by one nucleobase, consequently four exposure steps and thus 4 photomasks are required.

Due to the high parallelism in processing, this method is very rapid and efficient, and because of the high precision that can be achieved with photolithography, it is very well suited for the purpose of obtaining very high grid densities.

A review of the prior art in oligomer array production can be derived also from a special edition of Nature Genetics that appeared in January 1999 (Nature Genetics Supplement, Volume 21, January 1999) and the literature cited therein.

Patents, which generally refer to the use of oligomer arrays and photolithographic mask design, are, e.g., U.S. Pat. No. 5,837,832; U.S. Pat. No. 5,856,174; WO-A 98/27430 and U.S. Pat. No. 5,856,101. Several material and method patents also exist, which limit the use of photolabile protective groups to nucleosides, thus, e.g., WO-A 98/39348 and U.S. Pat. No. 5,763,599.

Various methods exist for immobilizing DNA. The best known method is the solid binding of a DNA, which is functionalized with biotin, to a streptavidin-coated surface. The binding strength of this system corresponds to a covalent chemical bond without being one. In order to be able to covalently bond a target DNA to a chemically pre-prepared surface, an appropriate functionality of the target DNA is required. DNA itself possesses no functionalization that is suitable. There are various procedures for introducing a suitable functionalization in a target DNA: two easy-to-manipulate functionalizations are primary, aliphatic amines and thiols. Such amines are quantitatively reacted with N-hydroxysuccinimide esters and thiols react under suitable conditions in a quantitative manner with alkyl iodides. It is difficult, however, to introduce such a functionalization in a DNA. The simplest variant is introducing one by means of a primer of a PCR. Presented variants utilize 5'-modified primers ($NH_2$ and SH) and a bifunctional linker.

An essential component of immobilization on a surface is the nature of the surface. Systems that have been described up until now are primarily comprised of silicon or metal (magnetic beads). Another method for binding a target DNA is based on using a short recognition sequence (e.g., 20 bases) in the target DNA for hybridizing to a surface-immobilized oligonucleotide.

As probes, which are fixed in an oligomer array on a surface, oligonucleotides are considered, but any modification of nucleic acids is also possible, e.g., peptide nucleic acids (PNAs), (Nielsen, P. E., Buchardt, O., Egholm, M. and Berg, R. H. 1993. Peptide nucleic acids. U.S. Pat. No. 5,539,082; Buchardt, O., Egholm, M. Berg, R. H. and Nielsen, P. E. 1993. Peptide nucleic acids and their potential applications in biotechnology. Trends in Biotechnology, 11: 384–386), phosphorothioate oligonucleotides or methylphosphonate oligonucleotides. The specificity of a probe is most essential. Peptide nucleic acids have an uncharged backbone, which at the same time deviates chemically very much from the familiar sugar-phosphate structure of the backbone in nucleic acids. The backbone of a PNA has an amide sequence instead of the sugar-phosphate backbone of the usual DNA. PNA hybridizes very well with DNA of complementary sequence. The melting point of a PNA/DNA hybrid is higher than that of the corresponding DNA/DNA hybrid and the dependence of hybridization on buffer salts is relatively small.

Matrix-assisted laser desorption/ionization mass spectrometry (MALDI) is a novel, very powerful development for analysis of biomolecules (Karas, M. and Hillenkamp, F. 1988. Laser desorption ionization of proteins with molecular masses exceeding 10,000 daltons. Anal. Chem. 60: 2299–2301). An analyte molecule is embedded in a matrix absorbing in the UV. The matrix is vaporized in vacuum by a short laser pulse and the analyte is thus transported unfragmented into the gas phase. An applied voltage accelerates the ions in a field-free flight tube. Ions are accelerated to a varying degree on the basis of their different masses. Smaller ions reach the detector sooner than larger ions and the flight time is converted into the mass of the ions.

The object of the present invention is to prepare oligomer arrays, which are particularly suitable for the detection of cytosine methylations.

The object is solved according to the invention in that an oligomer array is created with PNAs (peptide nucleic acids) and/or DNA oligomers on a surface, comprising oligomers of between 6 and 20 monomers or nucleobases each, whereby these comprise at least one sequence of the general formula DDCGDD or of the general formula DDTGDD, or of the general formula HHCGHH or of the general formula HHCAHH, wherein H indicates one of the bases adenine (A), cytosine (C), or thymine (T), and D represents one of the bases adenine (A), guanine (G) or thymine (T), and wherein the site of the oligomers on the surface is correlated with the sequence of the oligomers.

It is preferred according to the invention that at least 10% of the oligonucleotides contain a sequence of the general formula DDCGDD or of the general formula DDTGDD or of the general formula HHCGHH or of the general formula HHCAHH.

It is also preferred according to the invention that at least 25% of the oligonucleotides contain a sequence of the general formula DDCGDD or of the general formula DDTGDD or of the general formula HHCGHH or of the general formula HHCAHH.

It is also preferred according to the invention that at least 50% of the oligonucleotides contain a sequence of the general formula DDCGDD or of the general formula DDTGDD or of the general formula HHCGHH or of the general formula HHCAHH.

It is also preferred according to the invention that at least 75% of the oligonucleotides contain a sequence of the general formula DDCGDD or of the general formula DDTGDD or of the general formula HHCGHH or of the general formula HHCAHH.

It is preferred according to the invention that the surface is planar and the oligomers are arranged thereon in a rectangular or hexagonal grid, which permits assignment to coordinates. However, other appropriate geometric arrangements also can be selected, which help improve possibilities for automation, such as, for example, circular arrangements.

An oligomer array comprising sequences of the general formula DDCGDD and of the general formula DDTGDD and of the general formula HHCGHH and of the general formula HHCAHH is preferred.

Particularly preferred is an oligomer array comprising sequences of the general formula DDCGDD and of the general formula DDTGDD or sequences of the general formula HHCGHH and of the general formula HHCAHH.

It is preferred that the array comprises at least 100 different oligomers.

An oligomer array according to the invention is preferred, which is characterized in that, fitted to each oligomer, which contains a CG sequence, an analogous oligomer is immobilized, which is distinguished from said [CG] oligomer only by the fact that it contains a TG or a CA sequence, instead of the CG sequence.

It is further preferred that the surface is [made] of glass.

It is also preferred that the surface is [made] of metal or another conductive material. Most particularly preferred is a surface, which is the target of a MALDI mass spectrometer.

The present invention thus describes oligomer arrays, which can be used for the detection of the state of methylation of genomic DNA samples.

Another subject of the present invention is thus the use of an oligomer array according to the invention for hybridizing DNA fragments after a preceding amplification.

It is particularly preferred that DNA is treated with a bisulfite solution (or hydrogen sulfite solution, disulfite solution) prior to the amplification.

Another subject of the present invention is also the use of an oligomer array according to the invention for the detection of cytosine methylations in genomic DNA.

The subject of the present invention is thus an arrangement, preferably in the form of an oligomer array, of PNAs (peptide nucleic acids) or DNA oligomers on a surface, comprising oligomers of between 6 and 20 monomers (or nucleobases) each, which in turn contain sequences of the general formula DDCGDD and/or of the general formula DDTGDD and/or of the general formula HHCGHH and/or of the general formula HHCAHH, whereby the site of the oligomers on the surface each time permits a conclusion with respect to its sequence(s). Oligomer arrays of this type are particularly suitable for the detection of cytosine methylations in genomic DNA. The above-listed sequences hybridize to varying degrees, depending on the methylation status of the DNA after its chemical pretreatment with bisulfite.

In order to be able to better assign the signals coming from these hybridizations to the oligomer sequence utilized, it is particularly preferred that the surface is planar and the oligomers are arranged thereon in a rectangular or hexagonal grid, which permits assignment to coordinates.

Particularly preferred is an arrangement of PNAs (peptide nucleic acids)— or DNA oligomers on a surface, comprising oligomers of between 6 and 20 monomers (or nucleobases) each, containing sequences of the general formula DDCGDD and of the general formula DDTGDD and of the general formula HHCGHH and of the general formula HHCAHH, whereby the site of the oligomer on the surface each time permits a conclusion relative to its sequence(s).

Particularly preferred is an arrangement of PNAs (peptide nucleic acids) or DNA oligomers on a surface, each comprising oligomers of between 6 and 20 monomers (or nucleobases) of the general formula DDCGDD and of the general formula DDTGDD, whereby the site of the oligomers on the surface permits a conclusion to be made relative to its sequence(s) each time.

Particularly preferred is an arrangement of PNAs (peptide nucleic acids) or DNA oligomers on a surface, each comprising oligomers of between 6 and 20 monomers (or nucleobases) of the general formula HHCGHH and of the general formula HHCAHH, whereby the site of the oligomer on the surface each time permits a conclusion relative to its sequence(s).

It is also particularly preferred that the arrangement comprises at least 100 different oligomers, each of which contains at least one of the sequences DDCGDD, DDTGDD, HHCGHH or HHCAHH.

In a particularly preferred embodiment, the surface of the arrangement is [made] of glass. In another preferred embodiment, the surface of the arrangement is [made] of metal or another conductive material. In another particularly preferred embodiment, the arrangement is characterized in that the surface is the target of a MALDI mass spectrometer.

The subject of the present invention is also the use of an arrangement of PNAs (peptide nucleic acids) or DNA oligomers on a surface, each comprising oligomers of between 6 and 20 monomers (or nucleobases), which in turn contain sequences of the general formula DDCGDD and/or of the general formula DDTGDD and/or of the general formula HHCGHH and/or of the general formula HHCAHH, whereby the site of the oligomers on the surface each time permits a conclusion on their sequence(s), for hybridizing of DNA fragments, which have been previously amplified.

The use of DNA fragments, which have been prepared by means of the polymerase chain reaction is particularly preferred.

The use of an arrangement of PNA (peptide nucleic acids) or DNA oligomers on a surface, each comprising oligomers of between 6 and 20 monomers (or nucleobases), which in turn contain sequences of the general formula DDCGDD and/or of the general formula DDTGDD and/or of the general formula HHCGHH and/or of the general formula HHCAHH is also particularly preferred, whereby the site of the oligomers on the surface each time permits a conclusion on their sequence(s), for the hybridization of DNA, which has been previously treated with a bisulfite solution (or hydrogen sulfite, disulfite). The DNA has been amplified in a particularly preferred manner.

The use of an arrangement of PNA (peptide nucleic acids) or DNA oligomers on a surface, each comprising oligomers of between 6 and 20 monomers (or nucleobases), which in turn contain sequences of the general formula DDCGDD and/or of the general formula DDTGDD and/or of the general formula HHCGHH and/or of the general formula HHCAHH, is also particularly preferred, whereby the site of the oligomers on the surface each time permits a conclusion on their sequence(s) for the detection of cytosine methylations in genomic DNA.

The use according to the invention of oligomer arrays according to the invention for the detection of cytosine methylations in genomic DNA is explained, for example, in FIG. 1.

In FIG. 1, the letters H, D and N have the following meaning:

H represents one of the bases: adenine (A), cytosine (C) or thymine (T),

D represents one of the bases: adenine (A), guanine (G) or thymine (T) and

N represents one of the bases: adenine (A), guanine (G), cytosine (C) or thymine (T).

DNA sequences, which differ only in the methylation of cytosine, produce a modified sequence of nucleobases after treatment with bisulfite. The methylated cytosine is not changed by the bisulfite treatment, while the unmethylated cytosine is converted to thymine. After the amplification, this leads to different sequences, which then bind to different sites of the oligomer array, at which complementary sequences are present. Thus, since the sequences on the oligomer array are known, a conclusion on the methylation of the cytosine present in the original DNA is possible.

What is claimed is:

1. An oligomer array with PNA (peptide nucleic acids) and/or DNA oligomers on a surface, comprising at least 100 different oligomers of between 6 and 20 monomers or nucleobases, whereby at least 75% of said oligomers comprise at least one sequence of the general formula DDCGDD or of the general formula DDTGDD or of the general formula HHCGHH or of the general formula HHCAHH, wherein H indicates one of the bases: adenine (A), cytosine (C), or thymine (T) and D represents one of the bases: adenine (A), guanine (G) or thymine (T), and wherein the site of the oligomers on the surface is correlated with the sequence of the oligomers.

2. The oligomer array according to claim 1, further characterized in that the surface is planar and the oligomers are arranged thereon in a rectangular or hexagonal grid, which permits assignment to coordinates.

3. The oligomer array according to claim 1, comprising sequences of the general formula DDCGDD and of the general formula DDTGDD and of the general formula HHCGHH and of the general formula HHCAHH.

4. The oligomer array according to claim 1, comprising sequences of the general formula DDCGDD and of the general formula DDTGDD or sequences of the general formula HHCGHH and of the general formula HHCAHH.

5. The oligomer array according to claim 1, further characterized in that, for each oligomer; of said oligomer array which contains a first sequence comprising a CG dinucleotide, said oligomer array also includes an oligomer, which contains a second sequence that differs from said first sequence only by the fact that it contains a TG or a CA dinucleotide sequence instead of the CG sequence, said second sequence otherwise being identical to said first sequence.

6. The oligomer array according to claim 1, further characterized in that the surface is made of glass.

7. The oligomer array according to claim 1, further characterized in that the surface is made of metal or another conductive material.

8. Method for detection of DNA fragments comprising the steps of amplifying DNA fragments and hybridizing said amplified fragments to an oligomer array according to claim 1.

9. The method according to claim 8, further characterized in that the DNA is treated with a bisulfite solution or hydrogen sulfite solution or disulfite solution prior to the amplification of DNA fragments.

* * * * *